(12) United States Patent
Katagiri

(10) Patent No.: US 12,733,906 B2
(45) Date of Patent: Sep. 15, 2026

(54) CART FOR ULTRASOUND DIAGNOSTIC APPARATUS AND ULTRASOUND DIAGNOSTIC UNIT

(71) Applicant: FUJIFILM Corporation, Tokyo (JP)

(72) Inventor: Kengo Katagiri, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 19/077,028

(22) Filed: Mar. 11, 2025

(65) Prior Publication Data

US 2025/0295385 A1 Sep. 25, 2025

(30) Foreign Application Priority Data

Mar. 22, 2024 (JP) ................................ 2024-045887

(51) Int. Cl.
*A61B 8/00* (2006.01)

(52) U.S. Cl.
CPC .......... *A61B 8/4405* (2013.01); *A61B 8/4411* (2013.01); *A61B 8/4427* (2013.01)

(58) Field of Classification Search
CPC ... A61B 8/4405; A61B 8/4411; A61B 8/4427; A61B 8/4433
See application file for complete search history.

(56) References Cited

U.S. PATENT DOCUMENTS 9,180,898 B2 11/2015 Ninomiya et al.
2004/0262867 A1* 12/2004 Arceta ................ A61G 12/001 280/47.35
2011/0224544 A1* 9/2011 Ahn .................... A61B 8/4405 600/437
2017/0027541 A1* 2/2017 Henderson .......... A61B 8/4405

FOREIGN PATENT DOCUMENTS

| | | |
|---|---|---|
| JP | 2012065697 | 4/2012 |
| JP | 2013172777 | 9/2013 |
| JP | 2017000421 | 1/2017 |
| JP | 2017192502 | 10/2017 |
| WO | 2013046907 | 4/2013 |

* cited by examiner

*Primary Examiner* — Boniface N Nganga
(74) *Attorney, Agent, or Firm* — JCIPRNET

(57) ABSTRACT

A cart for an ultrasound diagnostic apparatus is provided. The cart includes a seat on which a portable ultrasound diagnostic apparatus is placed, a handle connected to the seat, a columnar support that supports the seat to be raisable and lowerable, a raising and lowering operation portion for raising and lowering the seat, a plurality of leg portions that support the columnar support, and a caster disposed on the leg portion. The handle includes a front handle disposed in front of the seat and a rear handle disposed behind the seat. The raising and lowering operation portion includes a front operation portion disposed below the front handle and a rear operation portion disposed below the rear handle.

8 Claims, 16 Drawing Sheets

CART FOR ULTRASOUND DIAGNOSTIC APPARATUS AND ULTRASOUND DIAGNOSTIC UNIT

CROSS-REFERENCE TO RELATED APPLICATION

This application claims priority under 35 USC 119 from Japanese Patent Application No. 2024-045887, filed 22 Mar. 2024, the disclosure of which is incorporated by reference herein.

BACKGROUND OF THE INVENTION

1. Field of the Invention

The present disclosure relates to a cart for an ultrasound diagnostic apparatus and an ultrasound diagnostic unit, and particularly to a technique for adjusting a height of a seat of the cart.

2. Description of the Related Art

An ultrasound diagnostic apparatus is used in an ultrasound examination of a living body. The ultrasound diagnostic apparatus is a medical apparatus that generates and displays an ultrasound image based on a received signal obtained by transmitting and receiving ultrasound waves. A tomographic image is known as a representative ultrasound image.

Portable ultrasound diagnostic apparatuses are being used. Examples of such portable ultrasound diagnostic apparatuses include a laptop type ultrasound diagnostic apparatus, which can be carried in a user's hand. In addition, the portable ultrasound diagnostic apparatuses are often used after being placed on a cart. A laptop type portable ultrasound diagnostic apparatus is moved to a position right beside a subject after being placed on a cart and the portable ultrasound diagnostic apparatus is opened and operated in a state where the portable ultrasound diagnostic apparatus is placed on the cart such that a probe is extended up to a subject and ultrasound waves are transmitted and received to and from the subject.

WO2013/046907, JP2012-65697A, JP2013-172777A, and JP2017-192502A disclose a cart (also referred to as a carriage) to which an ultrasound diagnostic apparatus is attachable and detachable. JP2017-421A discloses a configuration in which an intermediate seat is provided on a columnar support of a carriage, and a tablet computer as an auxiliary input device can be placed thereon, in relation to an ultrasound diagnostic system.

SUMMARY OF THE INVENTION

In a cart for an ultrasound diagnostic apparatus, the ultrasound diagnostic apparatus is placed on a seat. In a case where an operator operates the ultrasound diagnostic apparatus on the cart, the operator may want to adjust a height of the seat. In addition, in a case where the cart is transported to a place away from the original place, it may be desired to adjust the height of the seat. There is a demand for a cart in which the height of the seat can be easily adjusted.

An object of the present disclosure is to provide a cart for an ultrasound diagnostic apparatus or an ultrasound diagnostic unit, in which a height of a seat is easily adjustable.

A cart for an ultrasound diagnostic apparatus according to the present disclosure comprises a seat on which a portable ultrasound diagnostic apparatus is placed; a handle connected to the seat; a columnar support that supports the seat to be raisable and lowerable; a raising and lowering operation portion for raising and lowering the seat; a plurality of leg portions that support the columnar support; and casters disposed on the leg portions, in which the handle includes a front handle disposed in front of the seat and a rear handle disposed behind the seat, and the raising and lowering operation portion includes a front operation portion disposed below the front handle and a rear operation portion disposed below the rear handle.

An ultrasound diagnostic unit according to the present disclosure comprises the cart for an ultrasound diagnostic apparatus; and a portable ultrasound diagnostic apparatus placed on the seat of the cart.

According to the present disclosure, it is possible to easily adjust the height of the seat in the cart for an ultrasound diagnostic apparatus or the ultrasound diagnostic unit.

BRIEF DESCRIPTION OF THE DRAWINGS

FIG. 14 is a cross-sectional view showing the inside of the seat and showing an operative state of the unlocking pin by the rear operation portion.

DESCRIPTION OF THE PREFERRED EMBODIMENTS

Figure 1:
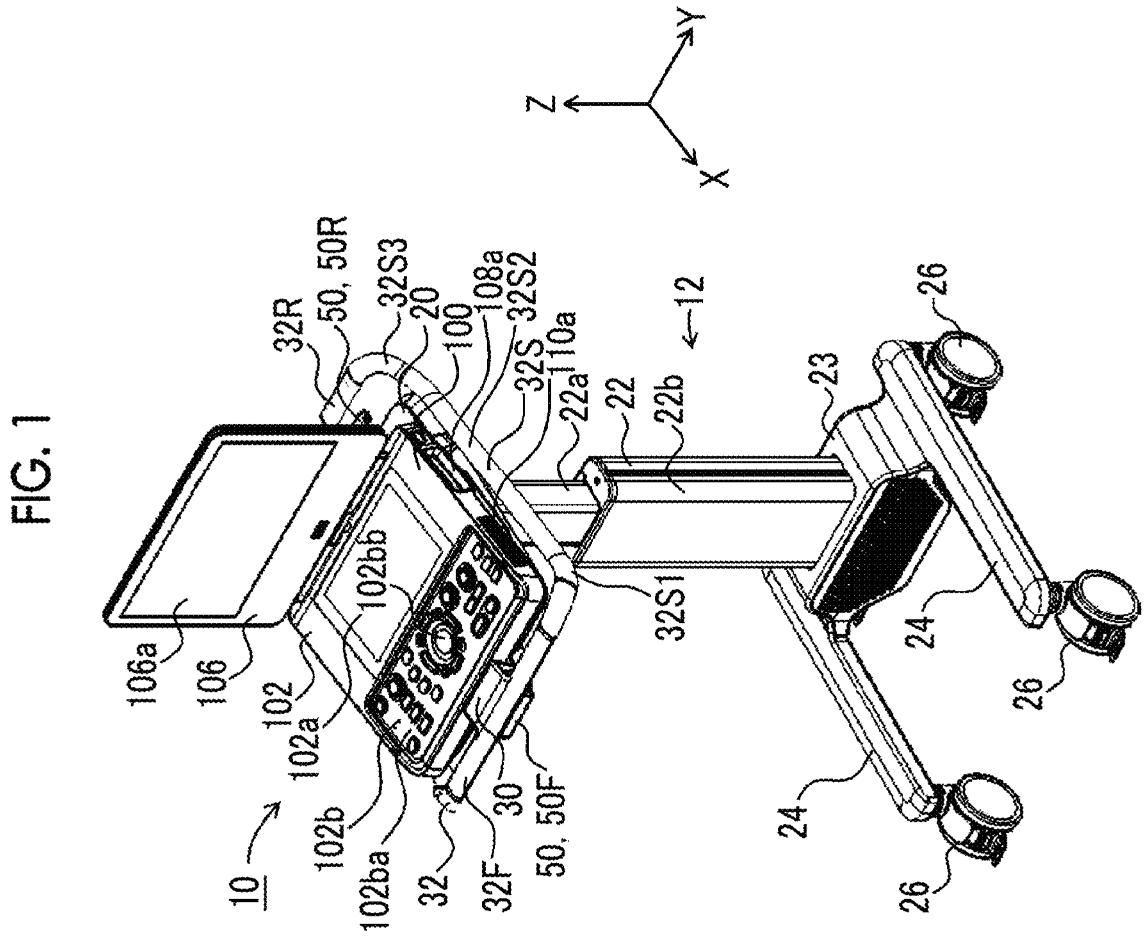
FIG. 1 is a perspective view of a front surface and a right side surface of an ultrasound diagnostic unit.

Hereinafter, the embodiment will be described with reference to the drawings. The present disclosure is not limited to the embodiment described herein. In all of the drawings, the same elements are denoted by the same reference numerals and the description thereof will not be repeated. In this specification, unless otherwise specified, directions represented by arrows X, Y, and Z in FIG. 1 will be referred to as "a forward direction", "a rightward direction", and "an upward direction", and directions opposite thereto will be referred to as "a rearward direction", "a leftward direction", and "a downward direction". A direction along the arrow Z coincides with a direction in which the gravity acts, that is, a vertical direction.

(1) Summary of Embodiment

A cart for an ultrasound diagnostic apparatus according to an embodiment comprises a seat on which a portable ultrasound diagnostic apparatus is placed, a handle connected to the seat, a columnar support that supports the seat to be raisable and lowerable, a raising and lowering operation portion for raising and lowering the seat, a plurality of leg portions that support the columnar support, and a caster disposed on the leg portion. The handle includes a front handle disposed in front of the seat and a rear handle disposed behind the seat. The raising and lowering operation portion includes a front operation portion disposed below the front handle and a rear operation portion disposed below the rear handle.

According to the above configuration, since the front operation portion is provided below the front handle, a user (for example, an operator) can easily adjust a height of the seat by operating the front operation portion with a finger in a state where a hand is placed on the front handle. In addition, since the rear operation portion is provided below the rear handle, the user (for example, an operator who transports the cart for an ultrasound diagnostic apparatus) can easily adjust the height of the seat by operating the rear operation portion with a finger in a state where the hand is placed on the rear handle.

In the embodiment, the front operation portion is a push-button disposed below the center of the front handle in the lateral direction. The seat locked to be unraisable and unlowerable is unlocked in a case where the push-button is pressed. Note that the expression "being locked to be unraisable and unlowerable" means a state where the seat is restricted from being raised and lowered and is locked such that the seat cannot be raised and lowered. The expression "the seat locked to be unraisable and unlowerable is unlocked" means that the seat is made raisable and lowerable.

According to a configuration as described above, a user (for example, an operator) can unlock the seat locked to be unraisable and unlowerable by pressing the push-button with a thumb in a state where a hand is placed on a left portion or a right portion of the front handle. In addition, the user also can unlock the seat locked to be unraisable and unlowerable by pressing the push-button with the thumbs of both hands in a state where both hands placed on the right and left portions of the front handle.

In the embodiment, the rear operation portion is a lever disposed below the rear handle. The seat locked to be unraisable and unlowerable is unlocked in a case where the lever is pulled up. With this configuration, for example, the user (for example, the operator of the cart) can pull up the lever with four fingers excluding the thumb in a state where the wrist is placed on the rear handle, and can unlock the seat locked to be unraisable and unlowerable.

In the embodiment, the lever that is the rear operation portion may include two lever elements. The two lever elements are disposed at interval in the lateral direction. The seat locked to be unraisable and unlowerable is unlocked by pulling up at least one of the two lever elements. With this configuration, the user (for example, the operator of the cart) can pull up one lever element with four fingers excluding the thumb in a state where the wrist is placed on a left portion or a right portion of the rear handle, and can unlock the seat locked to be unraisable and unlowerable. In addition, the user can pull up each of the two lever elements with each of both hands in a state where both wrists of both hands are placed on the left portion and right portion of the rear handle to unlock the seat locked to be unraisable and unlowerable.

In the embodiment, the columnar support includes an upper columnar support to which the seat is connected, a lower columnar support disposed below the upper columnar support, and a gas spring disposed therein. The columnar support has a structure that expands and contracts by inserting one of the upper columnar support and the lower columnar support into the other. One end of the gas spring is fixed to the seat, and the other end of the gas spring is fixed to the lower columnar support or a support body below the lower columnar support. The gas spring includes an unlocking pin. The gas spring fixes the seat to the lower columnar support in a non-operative state of the unlocking pin. That is, the seat is locked to be unraisable and unlowerable. The gas spring releases the fixation to the lower columnar support of the seat (unlocks the state of being locked to be unraisable and unlowerable) in an operative state of the unlocking pin, and biases the seat upward with respect to the lower columnar support. The front operation portion or the rear operation portion causes the unlocking pin to change from the non-operative state to the operative state by being operated.

According to the above-described configuration, in a case where the unlocking pin is changed to the operative state by the operation of the front operation portion or the rear operation portion, the descent of the seat can be suppressed, and the seat can be raised by a light force of the user.

In the embodiment, the handle comprises side handles disposed on the right and left sides of the seat. The handles are connected to each other so as to surround the seat. With this configuration, for example, the user can finely adjust the position of the cart or make the cart revolve while gripping the front handle or the rear handle with one hand and gripping the side handle with the other hand.

The ultrasound diagnostic unit according to the embodiment comprises the cart for an ultrasound diagnostic apparatus and a portable ultrasound diagnostic apparatus placed on a seat of the cart.

A cart for an ultrasound diagnostic apparatus according to another embodiment comprises a seat on which a portable ultrasound diagnostic apparatus is placed, a handle connected to the seat, a columnar support that supports the seat to be raisable and lowerable, a push-button for raising and lowering the seat, a plurality of leg portions that support the columnar support, and a caster disposed on the leg portion. The handle includes a front handle disposed in front of the seat. The push-button is disposed below the center of the handle in the lateral direction. The seat locked to be unraisable and unlowerable is unlocked in a case where the push-button is pressed.

According to a configuration as described above, a user (for example, an operator) can unlock the seat locked to be unraisable and unlowerable by pressing the push-button with a thumb in a state where a hand is placed on a left portion or a right portion of the front handle. In addition, the user (for example, the operator of the cart) can unlock the seat locked to be unraisable and unlowerable by extending the hand to the front of the cart and pressing the push-button in a case where the user is behind the cart.

In the cart for an ultrasound diagnostic apparatus according to another embodiment, the handle may comprise a side handle disposed on the right and left sides of the seat, and a rear handle disposed behind the seat.

An ultrasound diagnostic unit according to another embodiment comprises the cart for an ultrasound diagnostic apparatus according to the above-described another embodiment and a portable ultrasound diagnostic apparatus placed on a seat of the cart.

(2) Details of Embodiment

Figure 2:
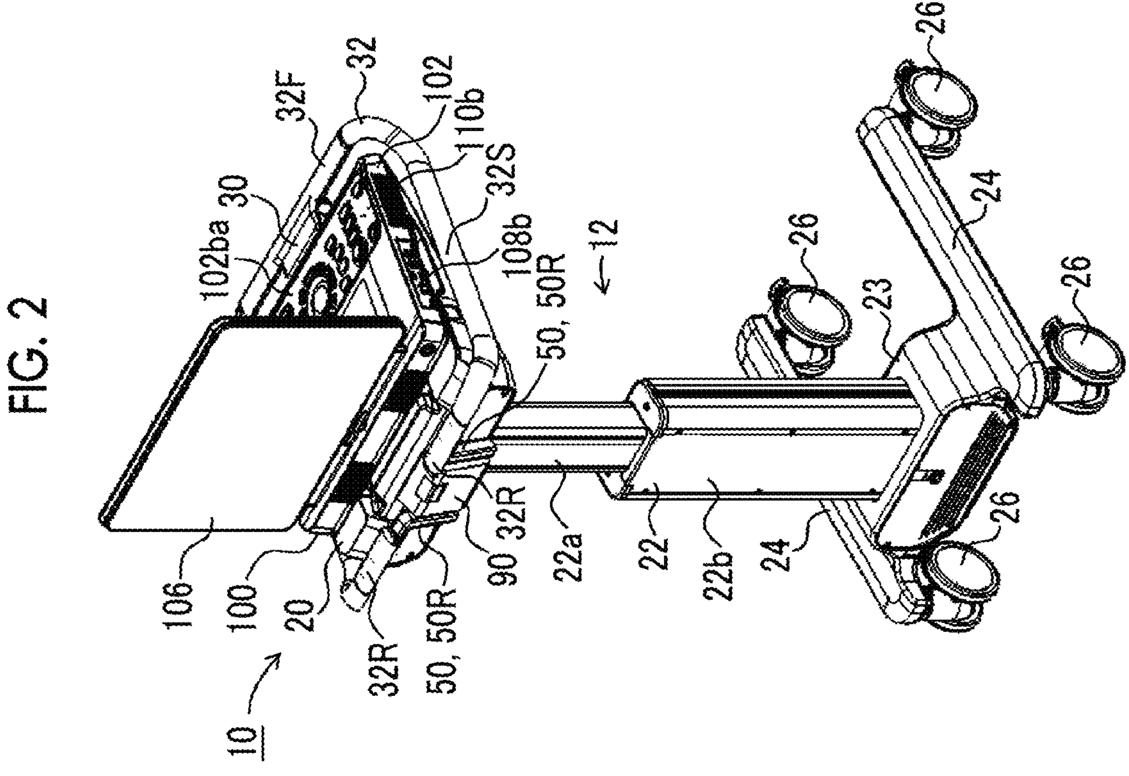
FIG. 2 is a perspective view of a rear surface and a left side surface of the ultrasound diagnostic unit.
Figure 3:
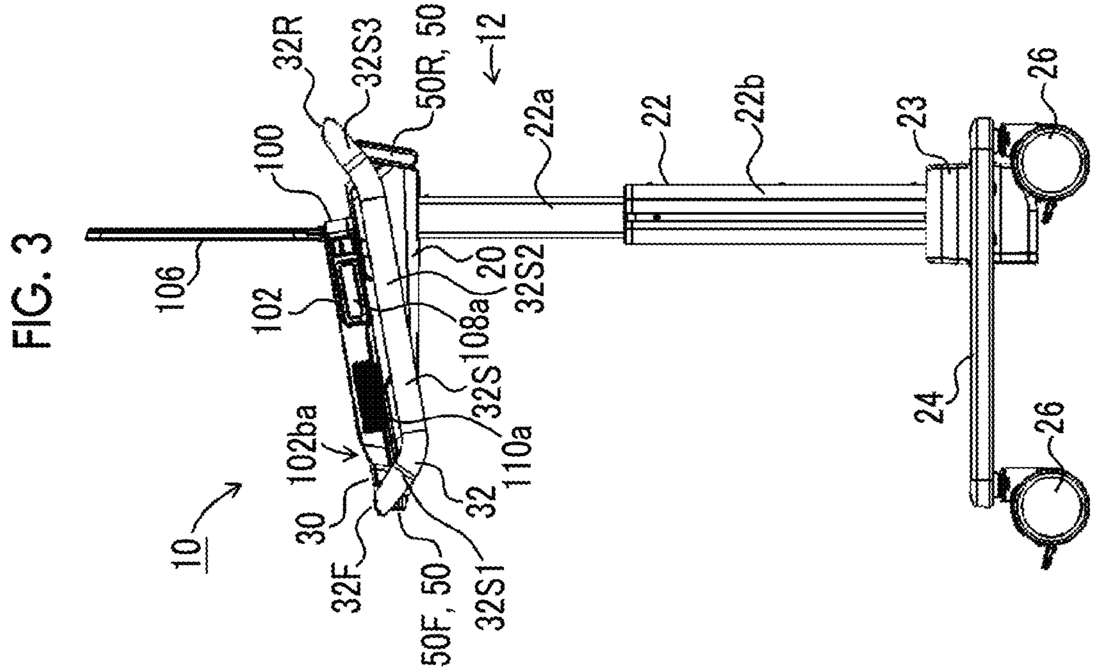
FIG. 3 is a right-side view of the ultrasound diagnostic unit.
Figure 4:
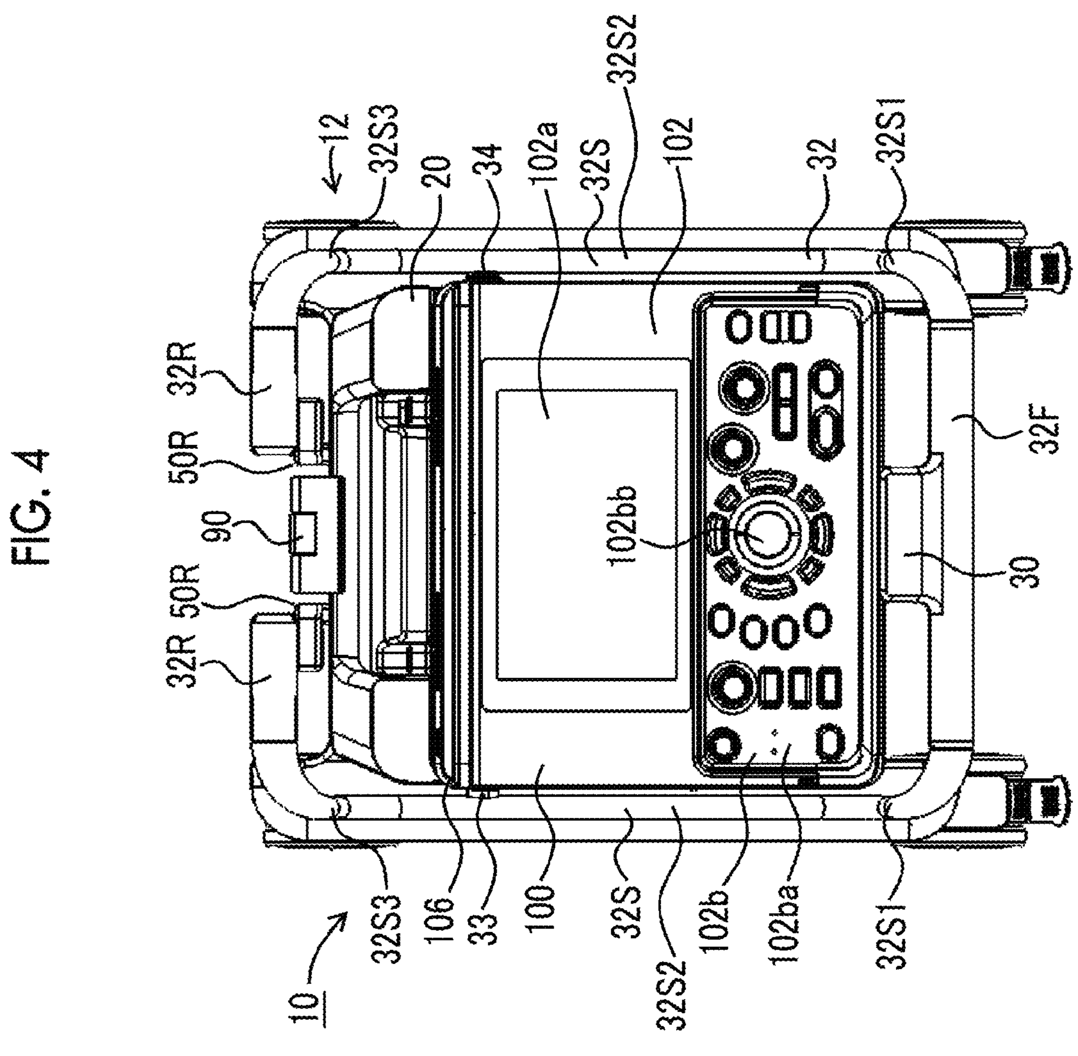
FIG. 4 is a plan view of the ultrasound diagnostic unit.

FIG. 1 shows an ultrasound diagnostic unit 10 according to the embodiment. The ultrasound diagnostic unit is installed in a medical institution such as a hospital and is used for an ultrasound examination of a subject. FIG. 1 is a perspective view of a front surface and a right side surface of an ultrasound diagnostic unit 10. FIG. 2 is a perspective view of a rear surface and a left side surface of the ultrasound diagnostic unit 10. FIG. 3 is a right-side view of the ultrasound diagnostic unit 10. FIG. 4 is a plan view of the ultrasound diagnostic unit 10.

Figure 5:
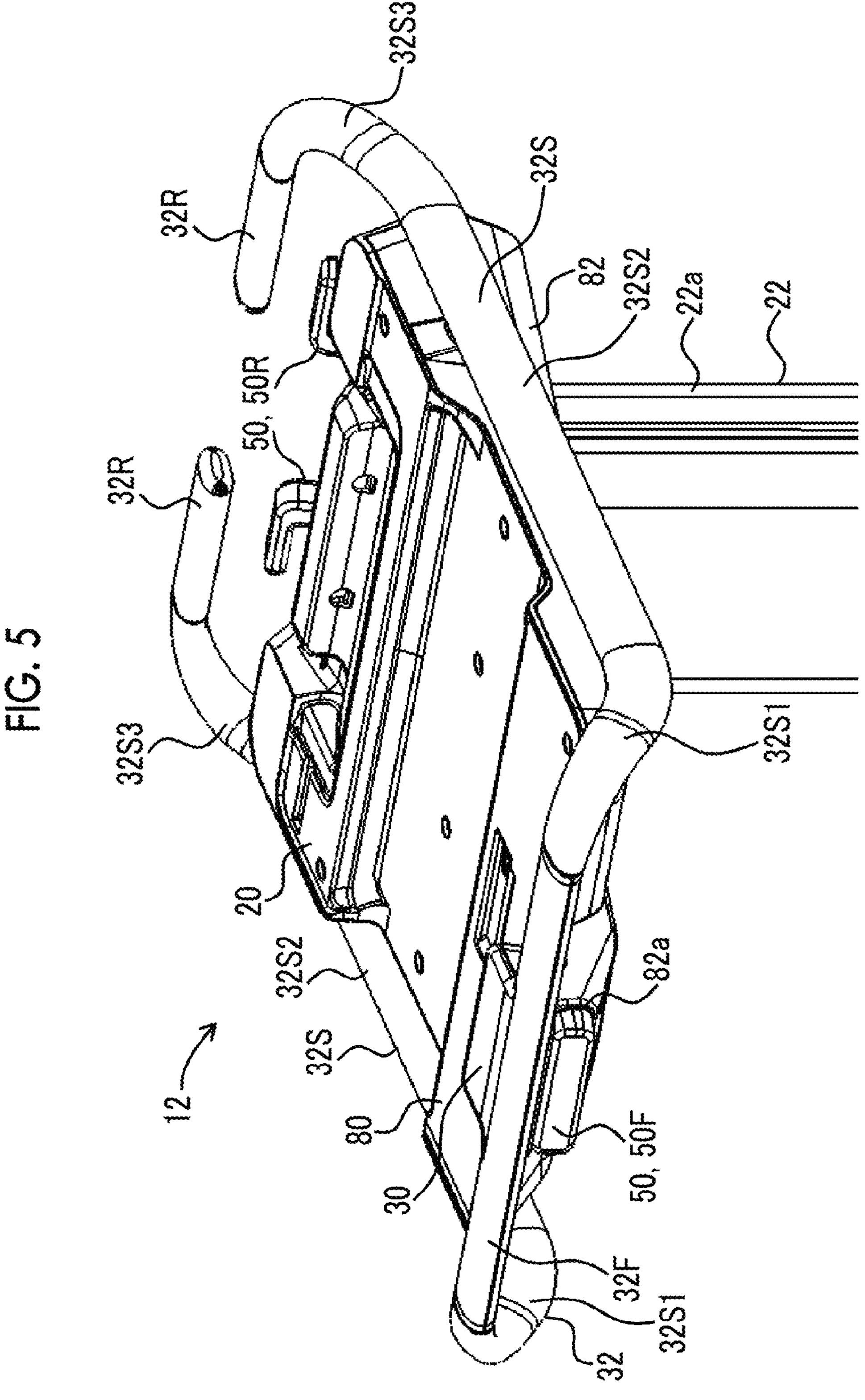
FIG. 5 is a perspective view of a front surface and a right side surface of an upper portion of a cart for an ultrasound diagnostic apparatus.
Figure 6:
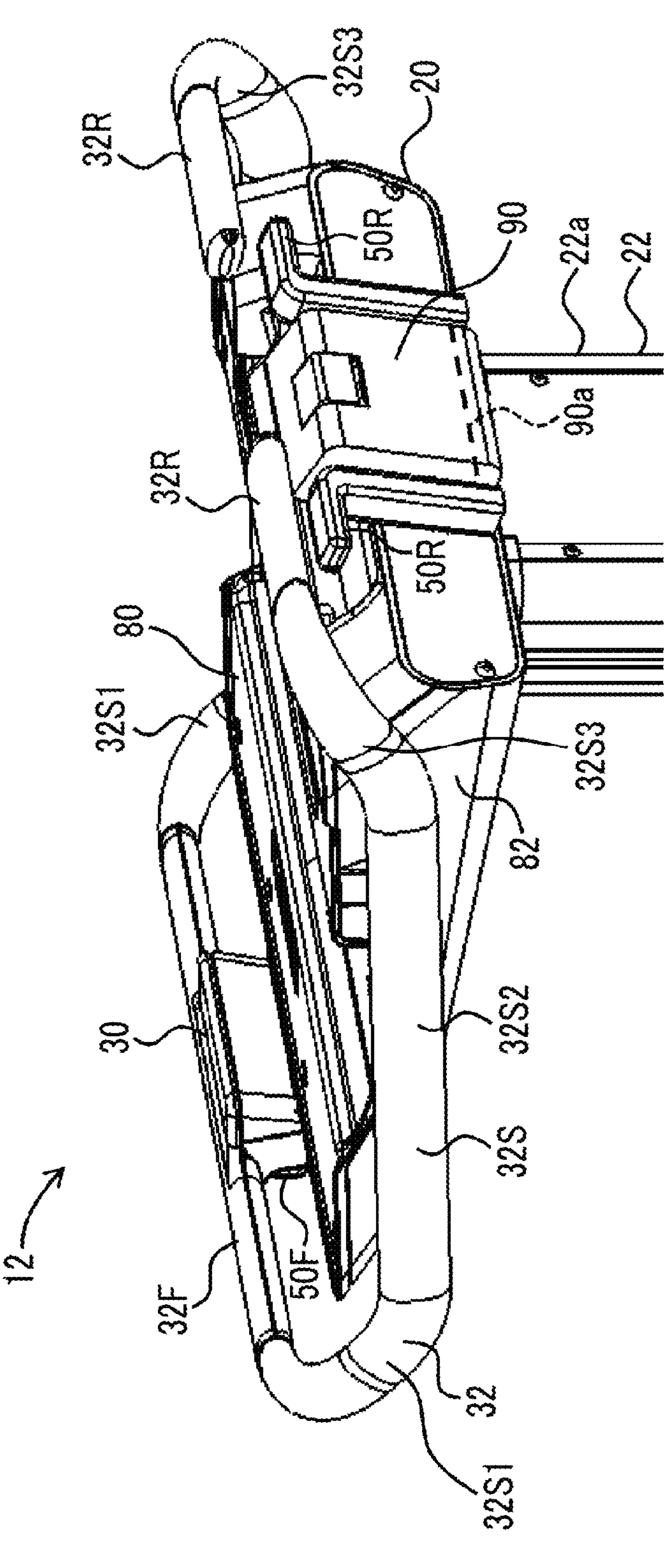
FIG. 6 is a perspective view of a rear surface and a right side surface of an upper portion of the cart for an ultrasound diagnostic apparatus.

The ultrasound diagnostic unit 10 comprises a cart 12 for an ultrasound diagnostic apparatus and a portable ultrasound diagnostic apparatus 100 (hereinafter, referred to as an ultrasound diagnostic apparatus 100) placed on a seat 20 of the cart 12. The ultrasound diagnostic apparatus 100 is attachably and detachably mounted on a seat 20 of the cart 12. FIGS. 5 and 6 show an upper portion of the cart 12 in a state in which the ultrasound diagnostic apparatus 100 is detached.

As shown in FIG. 1, the ultrasound diagnostic apparatus 100 is a laptop type. The ultrasound diagnostic apparatus 100 comprises an operation portion 102 and a display portion 106. The operation portion 102 and the display portion 106 are connected to each other by a hinge. The display portion 106 can be closed toward the operation portion 102 about a hinge. In FIGS. 1 to 4, the display portion 106 is in an open state. The display portion 106 comprises a display main body **106*a* having a display unit that faces forward in a state in which the display portion 106** is opened.

The operation portion 102 comprises a touch panel **102*a* and a button portion 102*b*. The button portion 102*b* comprises an upper surface 102*ba*, a plurality of buttons, and a trackball 102*bb*. The plurality of buttons are indicated by a plurality of small squares, circles, or the like in FIG. 1. The trackball 102*bb* is positioned in the center in the lateral direction, and the user can operate the trackball 102*bb* in a state in which the wrist is placed on the palm rest 30. A connector portion 108*a* (port) to which a connector of the probe is connected and an air discharge portion 110*a* through which air for cooling the inside of the ultrasound diagnostic apparatus 100 is discharged are provided on a right-side portion of the operation portion 102. In addition, as shown in FIG. 2, a connector portion 108*b* (port) to which a connector of various machines is connected and another air discharge portion 110*b* are provided on a left-side portion of the operation portion 102**.

As shown in FIG. 1, the cart 12 comprises a seat 20, a handle 32, a columnar support 22, a raising and lowering operation portion 50, a support body 23, two leg portions 24, and four casters 26.

The handle 32 is connected to the seat 20. As shown in FIG. 4, the handle 32 comprises a front handle 32F disposed in front of the seat 20, side handles 32S disposed on the right and left sides of the seat 20, and a rear handle 32R disposed behind the seat 20. The handles 32 are connected to each other so as to surround the seat 20. With this configuration, for example, the user can finely adjust the position of the cart 12 or make the cart 12 revolve while gripping the front handle 32F or the rear handle 32R with one hand and gripping the side handle 32S with the other hand.

The rear handle 32R is cut out at a center portion in the lateral direction, and is divided in the lateral direction. The rear handle 32R consists of a left rear handle element 32R and a right rear handle element 32R. The left rear handle element 32R extends to the right side from an end portion of the left side handle 32S. The right rear handle element 32R extends to the left side from an end portion of the right side handle 32S.

As shown in FIG. 4, the handle 32 is bonded to the seat 20 by the palm rest 30 and two connection portions 33 and 34.

As shown in FIG. 1, the front handle 32F extends in the lateral direction. Both end portions of the front handle 32F are bent in a rearward and downward oblique direction to be connected to the side handle 32S. As shown in FIGS. 5 and 6, each of the right and left side handles 32S includes a front portion 32S1 that is connected to the front handle 32F and inclined rearward and downward, a main body portion 32S2 that extends rearward from a rear end of the front portion 32S1, and a rear portion 32S3 that extends rearward from a rear end of the main body portion 32S2. The main body portion 32S2 of the side handle 32S is inclined upward from the front toward the rear. The rear portion 32S3 of the side handle 32S is steeply inclined upward as compared with the main body portion 32S2. As shown in FIG. 4, an end portion of the rear portion 32S3 of the side handle 32S is bent inward in the lateral direction of the cart 12 and is connected to the rear handle element 32R. As shown in FIG. 3, the rear handle element 32R is provided at a position higher than the front handle 32F.

The cross-sectional outer shape of the handle 32 has a flat oval shape. The front handle 32F and the rear handle 32R are disposed such that flat surfaces of the front handle 32F and the rear handle 32R face a vertical direction. The two side handles 32S are disposed such that flat surfaces of the side handles 32S face a lateral direction.

As shown in FIG. 3, the columnar support 22 supports the seat 20 to be raisable and lowerable. The columnar support 22 comprises an upper columnar support **22*a* to which the seat 20 is connected, a lower columnar support 22*b* disposed below the upper columnar support 22*a*, and a gas spring 64 (see FIG. 7) disposed inside the upper columnar support 22*a* and the lower columnar support 22*b*. As shown in FIG. 1, the upper columnar support 22*a* has a smaller width and a smaller thickness in the front-rear direction than the lower columnar support 22*b*. The columnar support 22 has a structure that expands and contracts by inserting the upper columnar support 22*a* into the lower columnar support 22*b***.

As shown in FIG. 5, the raising and lowering operation portion 50 comprises a front operation portion 50F and a rear operation portion 50R. The front operation portion 50F is a push-button disposed below the front handle 32F. The push-button 50F is disposed below the center of the front handle 32F in the lateral direction. The rear operation portion 50R is a lever disposed below the rear handle 32R. In particular, in this embodiment, the rear operation portion 50R is two lever elements. The columnar support 22 locked to be unexpandable and uncontractable (locked to be unraisable and unlowerable) is unlocked by pressing the push-button 50F or the pulling up at least one of the two lever elements 50R, and the seat 20 can be raised and lowered.

According to this configuration, the operator can adjust the height of the seat 20 by pressing the push-button 50F with the thumb in a state where the hand is placed on, for example, the left portion or the right portion of the front handle 32F. The operator can adjust the height of the seat 20 by pressing the push-button 50F even in a state of being seated on the right side or the left side of the front side of the cart 12, for example. In addition, the operator of the cart 12 can adjust the height of the seat 20 by pulling up each of the two lever elements with each of both hands in a state where both wrists of both hands are placed on the two rear handle elements 32R, for example. The operator of the cart 12 can adjust the height of the seat 20 by operating the two lever elements 50R according to, for example, the height of the operator, and can grip the rear handle 32R to transport the cart 12.

As shown in FIG. 1, the support body 23 is disposed below the lower columnar support 22*b*. The two leg portions 24 are disposed at interval in the lateral direction and are connected to the support body 23. Each of the two leg portions 24 extends in the front-rear direction and supports the columnar support 22 via the support body 23. In each of the two leg portions 24, the casters 26 are disposed on bottom surfaces of both end portions of the leg portion 24 in the front-rear direction.

As shown in FIG. 6, the seat 20 comprises a binding operation portion 90 used to bind the ultrasound diagnostic apparatus 100 to the seat 20, the binding operation portion 90 being provided at a rear surface that faces a region below a gap region between the two rear handle elements 32R. The binding operation portion 90 is a member having a rectangular parallelepiped shape and comprises a rotational movement shaft 90*a* provided at a lower portion thereof. The binding operation portion 90 rotationally moves about the rotational movement shaft 90*a* to enter a non-binding state where an upper portion thereof is separated from the rear surface of the seat 20 or a binding state where the upper portion is close to the rear surface of the seat 20.

In a case where the ultrasound diagnostic apparatus 100 is to be mounted to the seat 20, first, the binding operation portion 90 is caused to enter the non-binding state. Then, a rear portion of the ultrasound diagnostic apparatus 100 is placed on the seat 20 in a state where a front portion of the ultrasound diagnostic apparatus 100 is inclined downward and the front portion is aligned with a specified position of a front portion of the seat 20. Thereafter, the state of the binding operation portion 90 is changed to the binding state. Accordingly, the ultrasound diagnostic apparatus 100 is bound to the seat 20. The front portion of the ultrasound diagnostic apparatus 100 is bound to the seat 20 via a structure (for example, a hook and a groove) that is partially hooked on the seat 20. In a case where the state of the binding operation portion 90 is changed from the non-binding state to the binding state, the rear portion of the ultrasound diagnostic apparatus 100 is bound to the seat 20 with a pin protruding from the seat 20 and inserted into a hole in a rear surface of the ultrasound diagnostic apparatus 100.

As shown in FIG. 5, the seat 20 comprises a palm rest 30 connected to the front handle 32F. As shown in FIG. 4, the palm rest 30 is disposed in front of the operation portion 102 of the ultrasound diagnostic apparatus 100 and in the center in the lateral direction. The palm rest 30 is positioned between the front handle 32F and the operation portion 102 of the ultrasound diagnostic apparatus 100. As shown in FIG. 3, the front handle 32F, the palm rest 30, and the upper surface 102*ba* of the operation portion of the ultrasound diagnostic apparatus form a continuous upper surface. As a result, the operator can operate the ultrasound diagnostic apparatus 100 by placing the wrist on the front handle 32F and the palm rest 30.

As shown in FIG. 5, the seat 20 comprises a housing 82 and a top plate 80 attached to the housing 82. The housing 82 is formed in a dish shape and has an inner space. FIGS. 7, 8, and 11 to 13 each show a part of the seat 20 (the inner space of the housing 82) in a state where the top plate 80 is detached. A mechanism for raising and lowering the seat 20 is disposed in the inner space of the housing 82.

Figure 7:
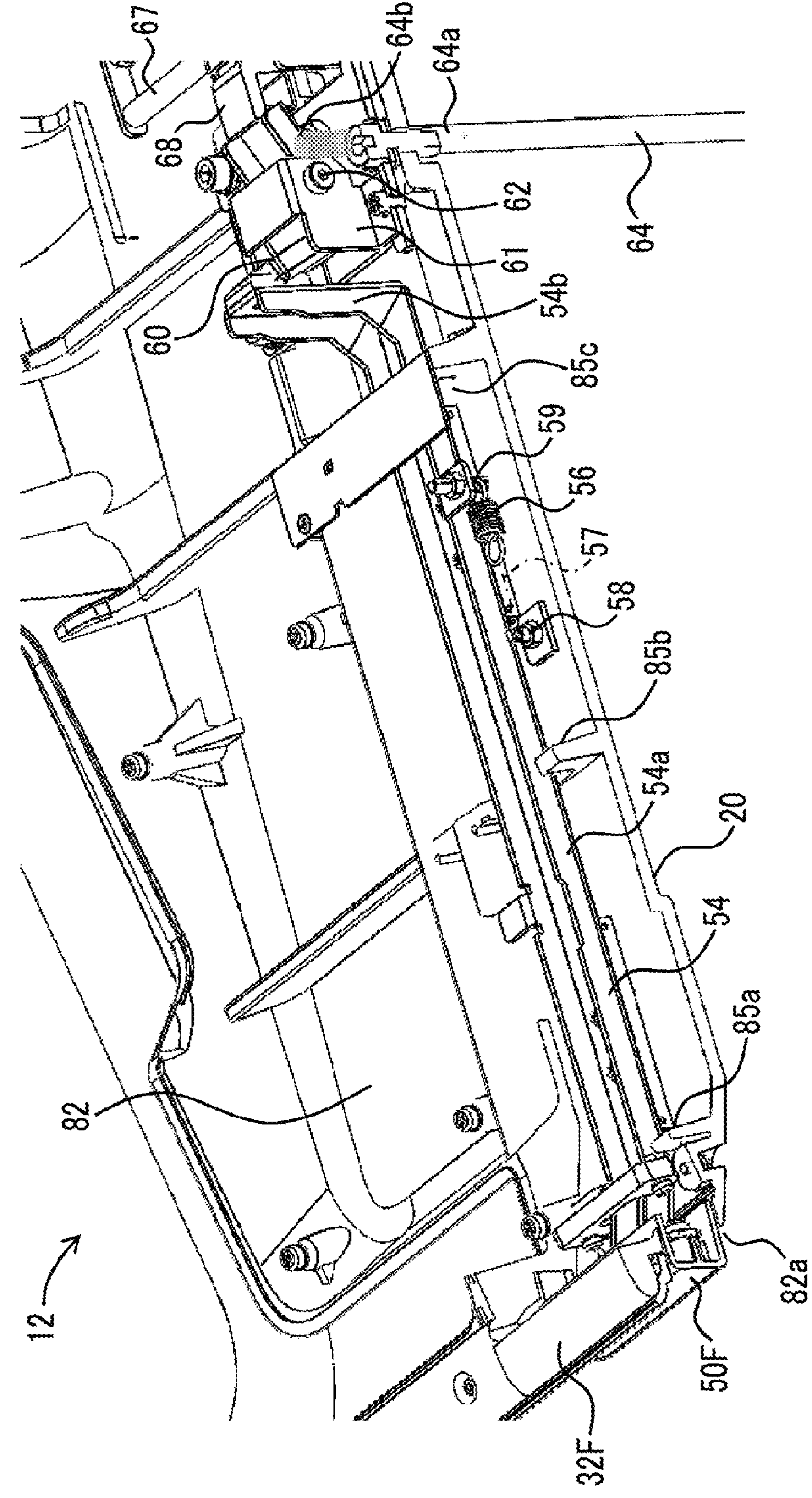
FIG. 7 is a perspective view showing an inside of a seat and showing a state in which a front operation portion is not operated.
Figure 9:
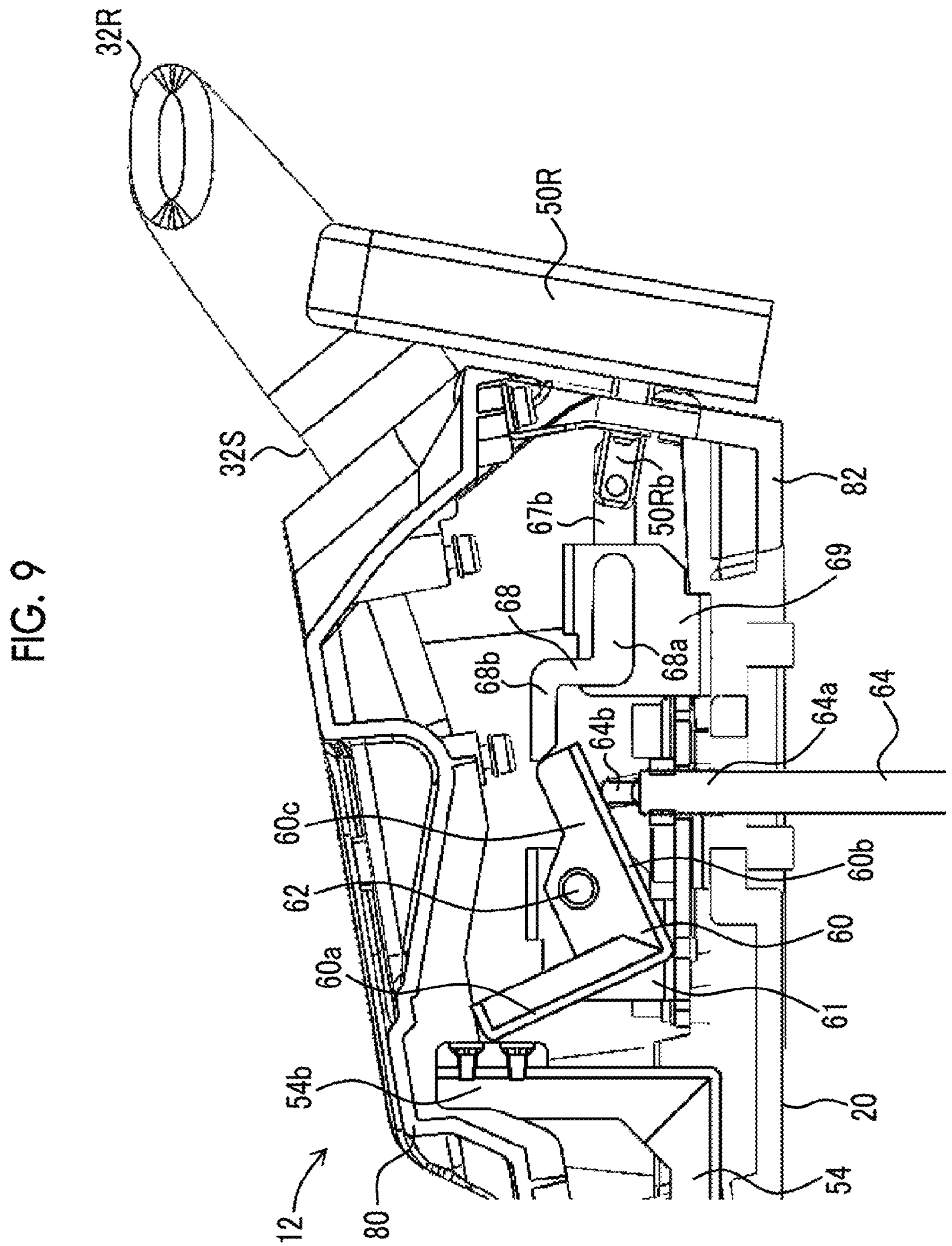
FIG. 9 is a cross-sectional view showing the inside of the seat and showing a non-operative state of an unlocking pin of a gas spring.

As described above, the gas spring 64 is disposed inside the columnar support 22. As shown in FIG. 7, one end of the gas spring 64 is fixed to the seat 20. The other end (not shown) of the gas spring 64 is fixed to the lower columnar support 22*b* (see FIG. 1) or the support body 23 below the lower columnar support 22*b*. As shown in FIG. 9, the gas spring 64 comprises an unlocking pin 64*b*. The gas spring 64 fixes the seat 20 to the lower columnar support 22*b* in a non-operative state of the unlocking pin 64*b* (see FIG. 9). The gas spring 64 releases the fixation of the seat 20 to the lower columnar support 22*b* in an operative state of the unlocking pin 64*b* (see FIGS. 10 and 14) and biases the seat 20 upward with respect to the lower columnar support 22*b*. The push-button 50F (front operation portion) or the two lever elements 50R (rear operation portion) is operated to change the unlocking pin 64*b* from the non-operative state to the operative state.

According to this configuration, in a case where the push-button 50F or the two lever elements 50R are operated, the seat 20 is biased upward with respect to the lower columnar support 22*b*, so that the unintended descent of the seat 20 can be suppressed and the seat 20 can be raised with a light force of the user. The user can lower the seat 20 by pushing down the seat 20 against the biasing of the gas spring 64 upward with respect to the seat 20 by operating the push-button 50F or the two lever elements 50R. In addition, the user can raise the seat 20 only by operating the push-button 50F or the two lever elements 50R or only by lightly lifting the seat 20 in addition to the operation.

Figure 8:
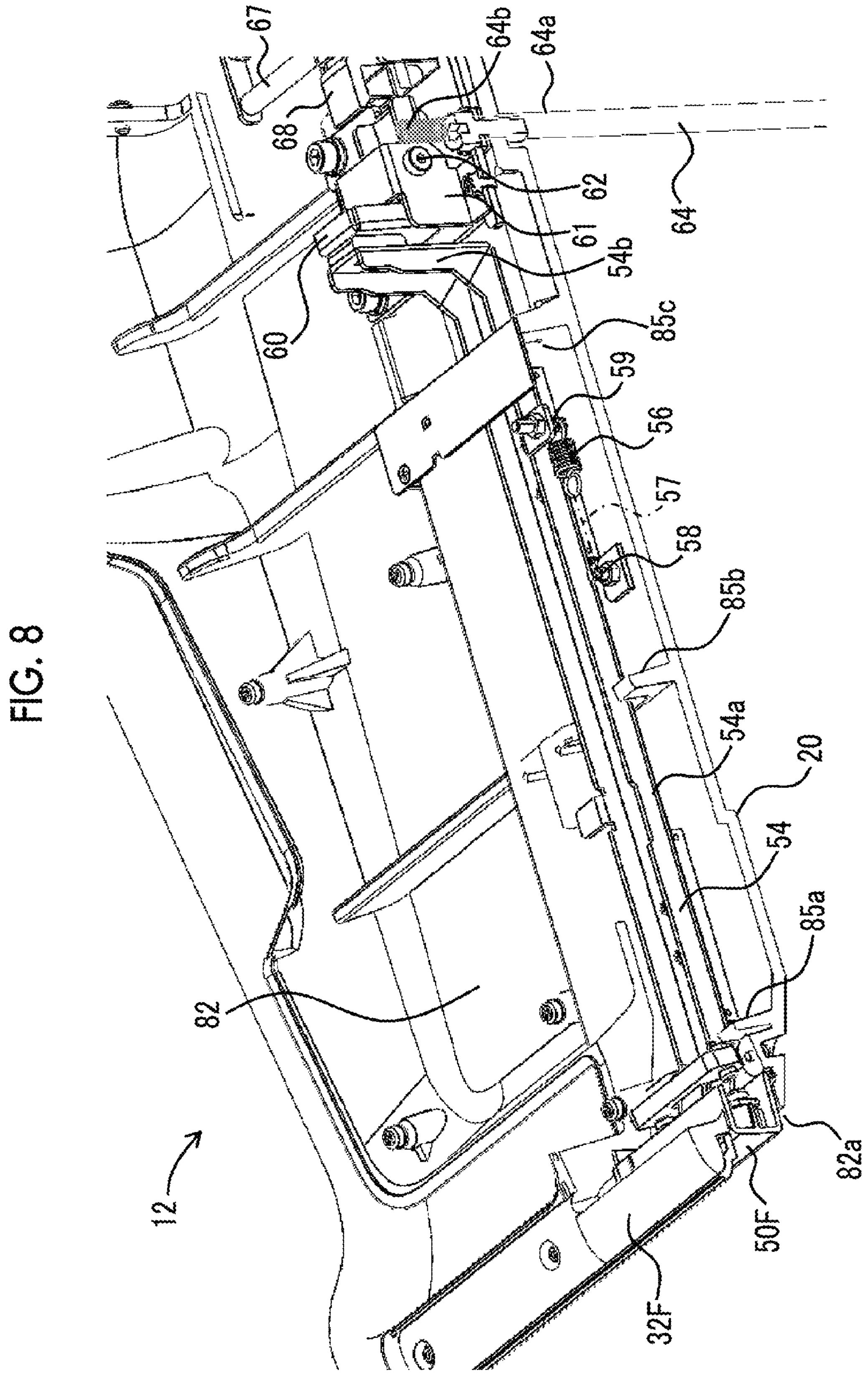
FIG. 8 is a perspective view showing the inside of the seat and showing a state in which a front operation portion is operated.

FIG. 7 shows the inside of the housing 82 in a state where the push-button 50F is not pressed. FIG. 8 shows the inside of the housing 82 in a state where the push-button 50F is pressed. The seat 20 comprises a link 54, a pin swinging body 60, and a holding portion 61 of the pin swinging body 60. The link 54 comprises a link main body 54*a* and a tip portion 54*b*. The link main body 54*a* is a member extending in the front-rear direction. The push-button 50F is connected to one end of the link main body 54*a*. A tip portion 54*b* is connected to the other end of the link main body 54*a*.

The housing 82 has a plurality of ribs on the bottom wall, and the support portions 85*a*, 85*b*, and 85*c* of the link main body 54*a* are formed by cutting out a part of each rib.

The seat 20 comprises a tension spring 56. One end of the tension spring 56 is connected to a connection portion 59 fixed to the link main body 54*a*. The other end of the tension spring 56 is connected to a fixing portion 58 fixed to the bottom wall of the housing 82. In FIGS. 7 and 8, for convenience of illustration, the other end of the tension spring 56 is connected to the fixing portion 58 via a one-dot chain line (denoted by reference numeral 57), but in practice, the other end of the tension spring 56 is directly connected to the fixing portion 58. Although not shown in FIGS. 7 and 8, the tension spring 56 is in a slightly stretched state regardless of the pressing of the push-button 50F. In addition, in a state where the push-button 50F is pressed (FIG. 8), the tension spring 56 is more stretched than in a state where the push-button 50F is not pressed (FIG. 7).

The push-button 50F is disposed in the hole 82*a* provided in the seat 20. The push-button 50F is biased forward by a tension spring 56 connected to the link main body 54*a*. The push-button 50F and the seat 20 have a restriction structure (for example, a hook structure formed of a protruding portion and a groove) that restricts excessive forward movement of the push-button 50F.

As shown in FIG. 8, in a case where the push-button 50F is pressed, the link 54 is moved forward, and the tip portion 54*b* of the link 54 pushes the pin swinging body 60. In addition, as shown in FIG. 7, in a case where the pressing of the push-button 50F is released, the push-button 50F returns to the initial position by the biasing force of the tension spring 56, and the tip portion 54*b* of the link 54 is in a state of not pushing the pin swinging body 60.

The pin swinging body 60 is disposed inside the holding portion 61. As shown in FIG. 9, the pin swinging body 60 has a substantially L-shape in a side view. The pin swinging body 60 comprises a front wall 60*a*, a bottom wall 60*b*, and two side walls 60*c* (only one is shown in FIG. 9) that are provided on the right and left sides. The two side walls 60*c* are provided with holes through which a shaft 62 extending in the lateral direction passes. The shaft 62 (see, for example, FIGS. 7 and 12) is fixed to two side walls of the holding portion 61. The pin swinging body 60 is capable of swinging about the shaft 62.

Figure 10:
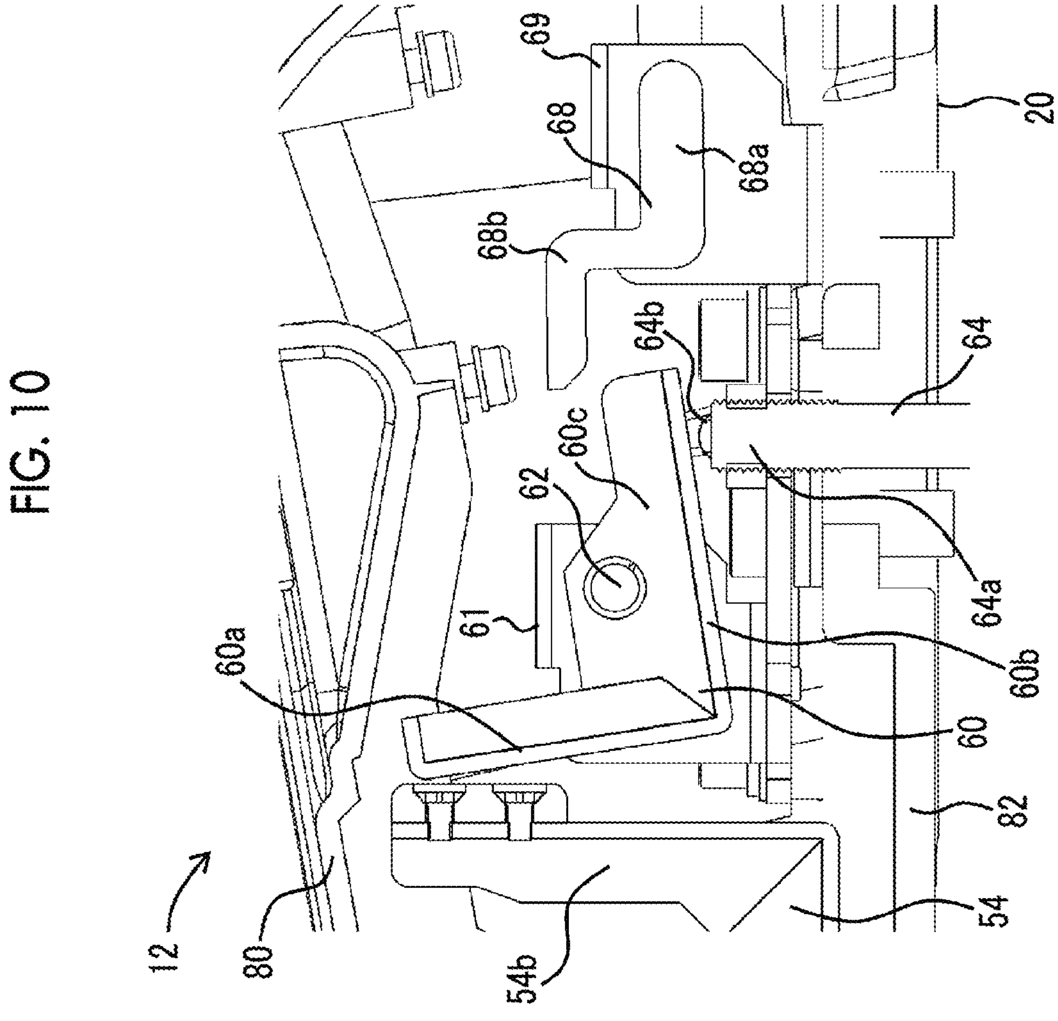
FIG. 10 is a cross-sectional view showing the inside of the seat and showing an operative state of the unlocking pin by the front operation portion.

As shown in FIG. 9, the gas spring 64 comprises an unlocking pin 64*b* and a sleeve portion 64*a* into which the unlocking pin 64*b* enters. The unlocking pin 64*b* is biased upward. As shown in FIG. 9, a state where the unlocking pin 64*b* protrudes upward is a non-operative state of the unlocking pin 64*b*. As shown in FIG. 10, a state where the unlocking pin 64*b* is retracted in the sleeve portion 64*a* is an operative state of the unlocking pin 64*b*.

As shown in FIG. 9, the pin swinging body 60 is in a posture inclined forward in which the bottom wall 60*b* is lifted by the unlocking pin 64*b* at the initial position. As shown in FIG. 8, in a case where the push-button 50F is pressed, the tip portion 54*b* of the link 54 pushes an upper portion of the front wall 60*a* (see FIG. 10) of the pin swinging body 60. Accordingly, as shown in FIG. 10, the pin swinging body 60 swings, and the bottom wall 60*b* of the pin swinging body 60 pushes the unlocking pin 64*b* to change the unlocking pin 64*b* to the operative state. That is, the unlocking pin 64*b* can be changed from the non-operative state to the operative state by pressing the push-button 50F.

In a case where the user stops pressing the push-button 50F (for example, releases the hand from the push-button 50F), the push-button 50F is returned to the initial position by the tension spring 56. Accordingly, the tip portion 54*b* of the link 54 returns to the front side (see FIG. 9), so that the pin swinging body 60 returns to the initial position (see FIG. 9), there by the unlocking pin 64*b* is in the non-operative state.

Figure 11:
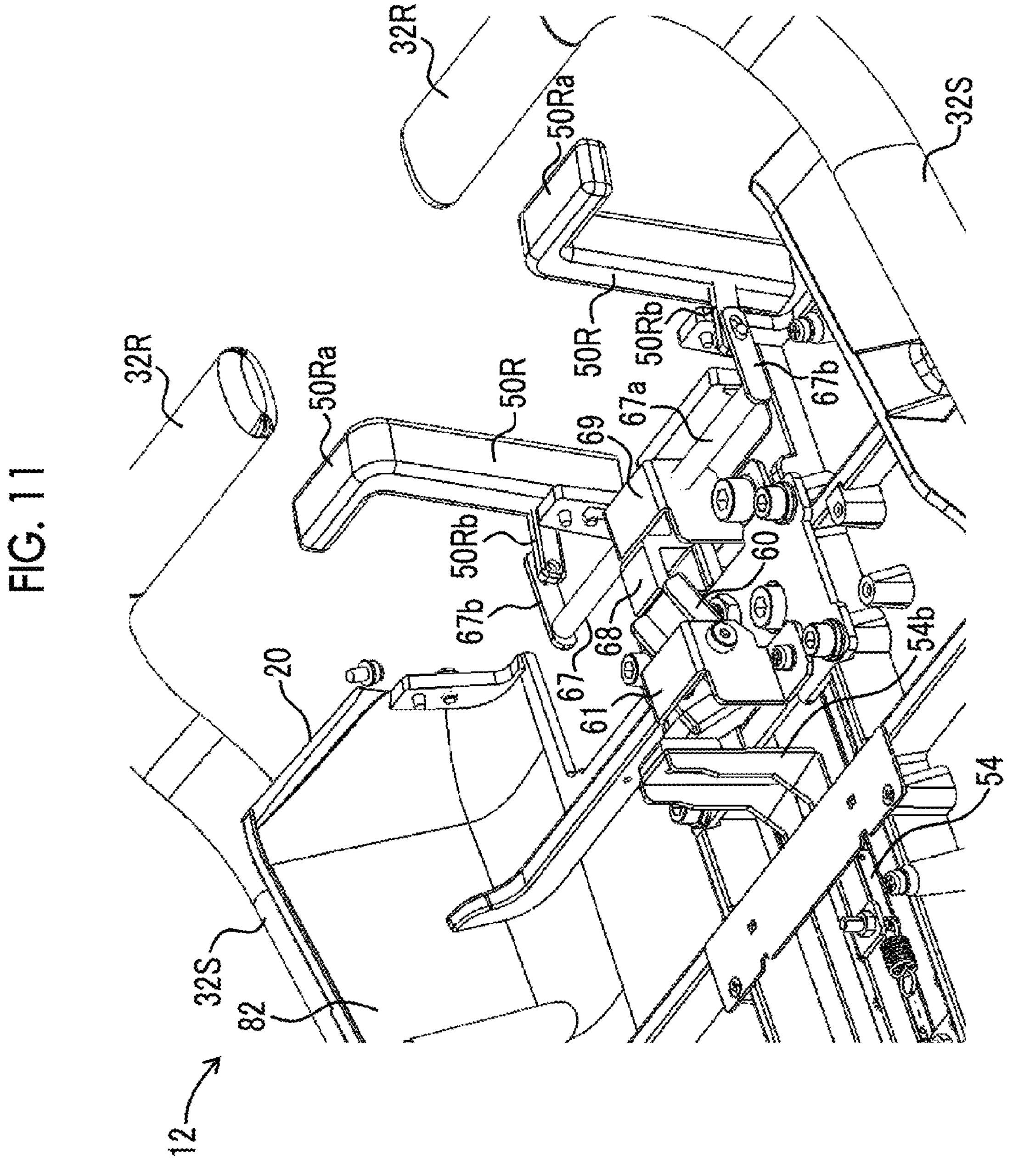
FIG. 11 is a perspective view showing the inside of the seat and showing a state in which the rear operation portion is not operated.
Figure 12:
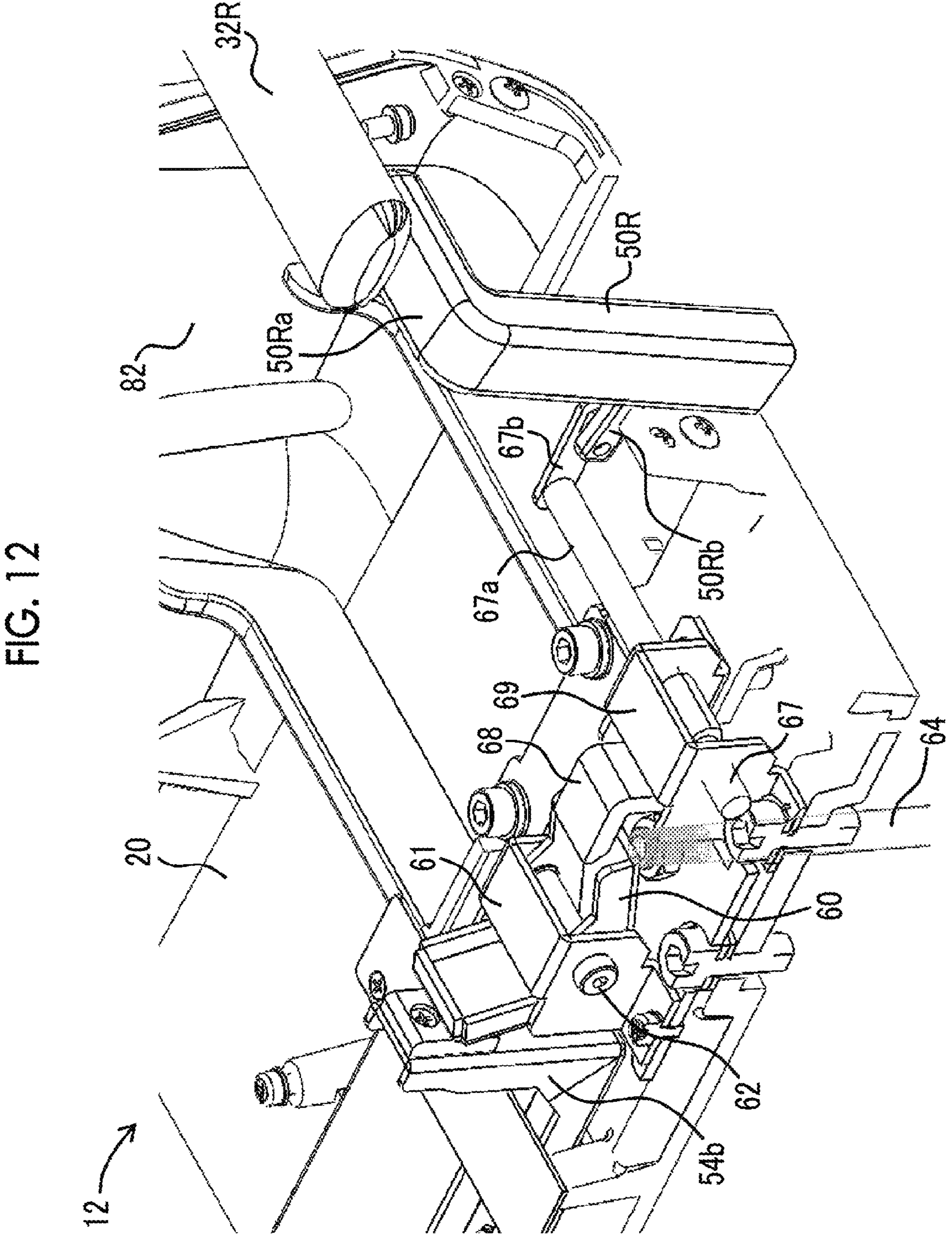
FIG. 12 is a perspective view showing the inside of a seat and showing a state in which the rear operation portion is not operated.
Figure 13:
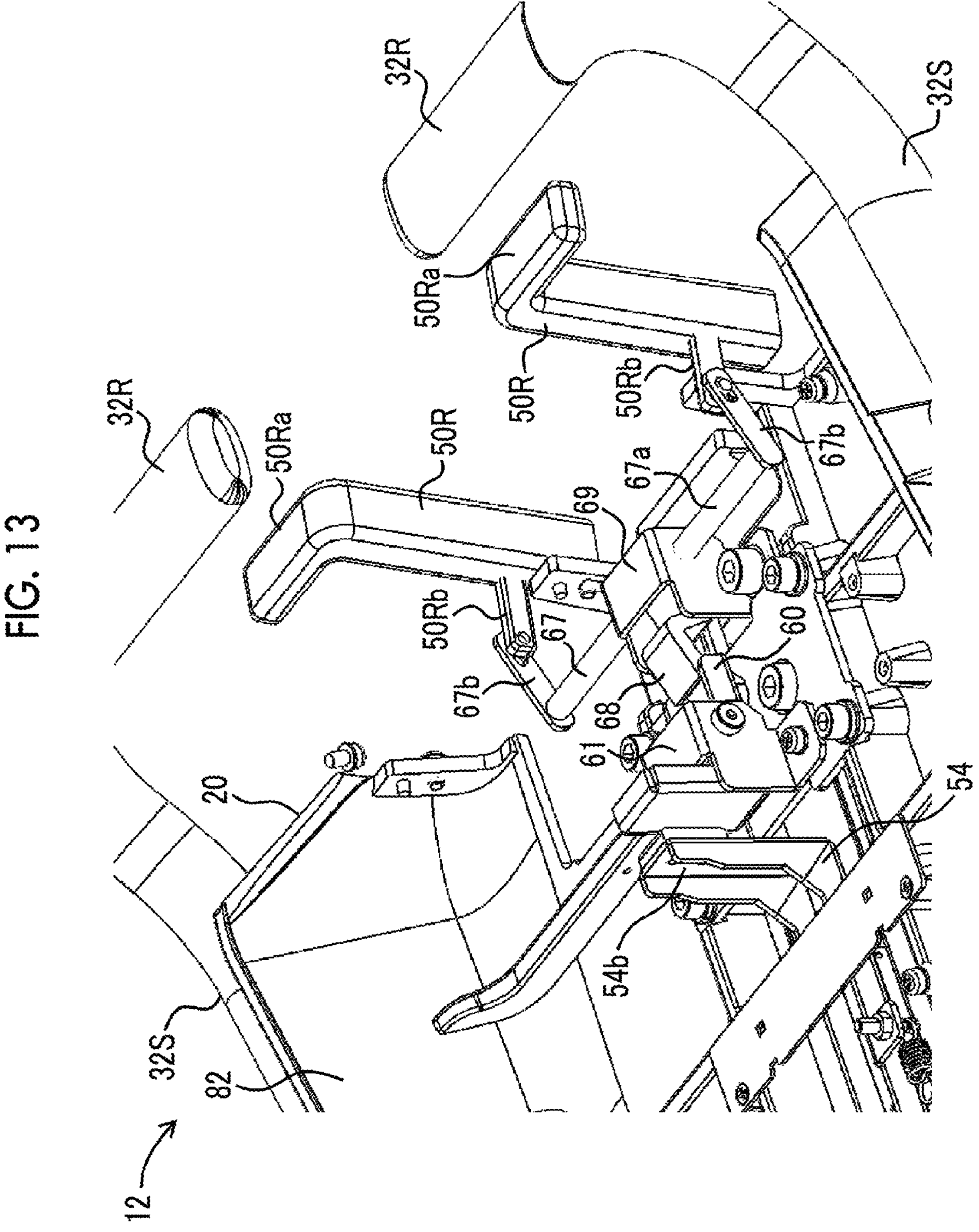
FIG. 13 is a perspective view showing the inside of the seat and showing a state in which the rear operation portion is operated.

FIGS. 11 and 12 show the inside of the housing 82 in a state where the two lever elements 50R are not being operated. FIG. 13 shows the inside of the housing 82 in a state where the two lever elements 50R are pulled up. Each of the two lever elements 50R comprises an operating portion 50Ra that is operated by the user and a connecting portion 50Rb. The seat 20 comprises a link 67, a holding portion 69 that holds the link 67, and a rear swinging body 68 that is coupled to the link 67.

The link 67 comprises a rotational movement shaft 67*a* extending in the lateral direction and two connecting portions 67*b* coupled to both ends of the rotational movement shaft 67*a*. The rearward tips of the two connecting portions 67*b* are rotationally movably connected to the tip of the connecting portion 50Rb of the two lever elements 50R. The rotational movement shaft 67*a* of the link 67 is passed through holes provided in the two side walls of the holding portion 69 and is held by the holding portion 69 so as to be rotationally movable.

The rear swinging body 68 is disposed inside the holding portion 69. The rear swinging body 68 comprises a base 68*a* (see FIG. 9) that is coupled to the rotational movement shaft 67*a* of the link 67 and a stepped portion 68*b* that is connected to the base 68*a*. The tip portion of the stepped portion 68*b* is positioned above the bottom wall 60*b* of the pin swinging body 60. In a state where the two lever elements 50R are not operated, the rear swinging body 68 is in an elevated posture as shown in FIG. 9.

Figure 14:
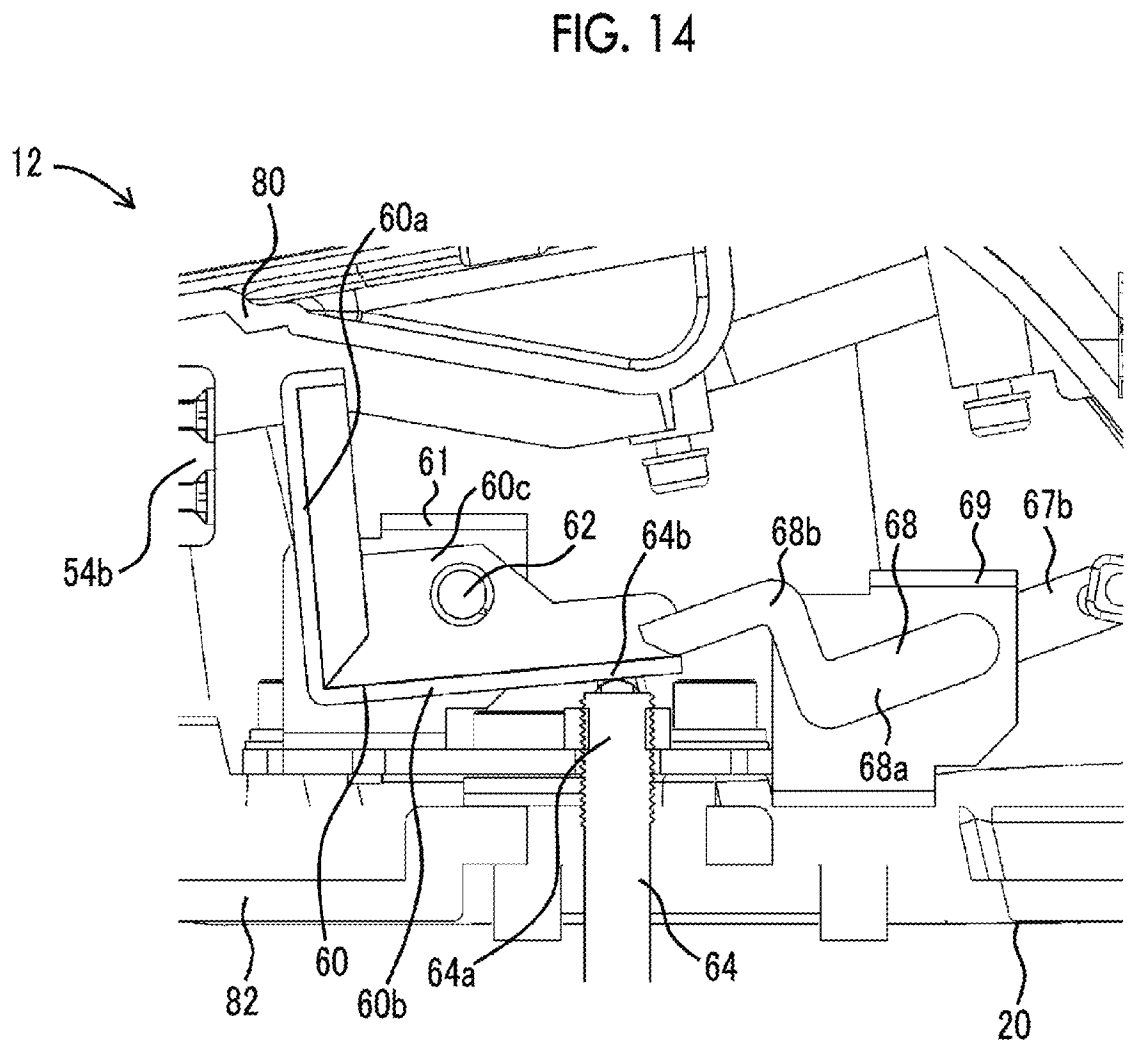

In a case where the two lever elements 50R are pulled up, as shown in FIG. 13, the two connecting portions 50Rb of the two lever elements 50R revolve the two connecting portions 67*b*, thereby causing the rotational movement shaft 67*a* to rotationally move. Accordingly, the rear swinging body 68 is in a fallen posture. As shown in FIG. 14, the tip portion of the stepped portion 68*b* of the rear swinging body 18 pushes down the bottom wall 60*b* of the pin swinging body 60. Accordingly, as shown in FIG. 14, the pin swinging body 60 swings, and the bottom wall 60*b* of the pin swinging body 60 pushes the unlocking pin 64*b* to change the unlocking pin 64*b* to the operative state. That is, the unlocking pin 64*b* can be changed from the non-operative state to the operative state by pulling up the two lever elements 50R.

In a case where the user releases their hand from the two lever elements 50R, the two lever elements 50R return to the initial position due to their own weight. Accordingly, the rear swinging body 68 returns to the elevated posture (see FIG. 9), so that the pin swinging body 60 returns to the initial position (see FIG. 9), and the unlocking pin 64*b* enters the non-operative state.

Figure 15:
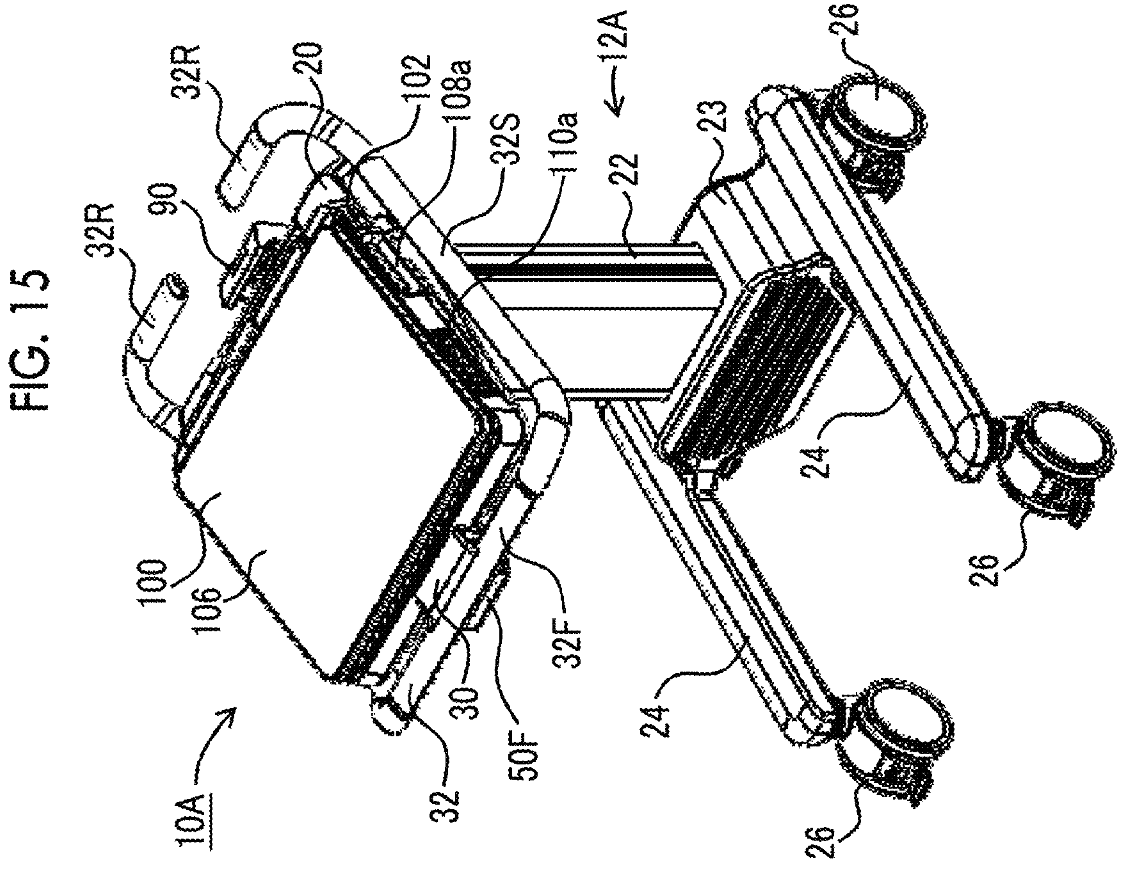
FIG. 15 is a perspective view of the front surface and right side surface of another ultrasound diagnostic unit, and showing a state in which a display portion of the ultrasound diagnostic apparatus is closed.
Figure 16:
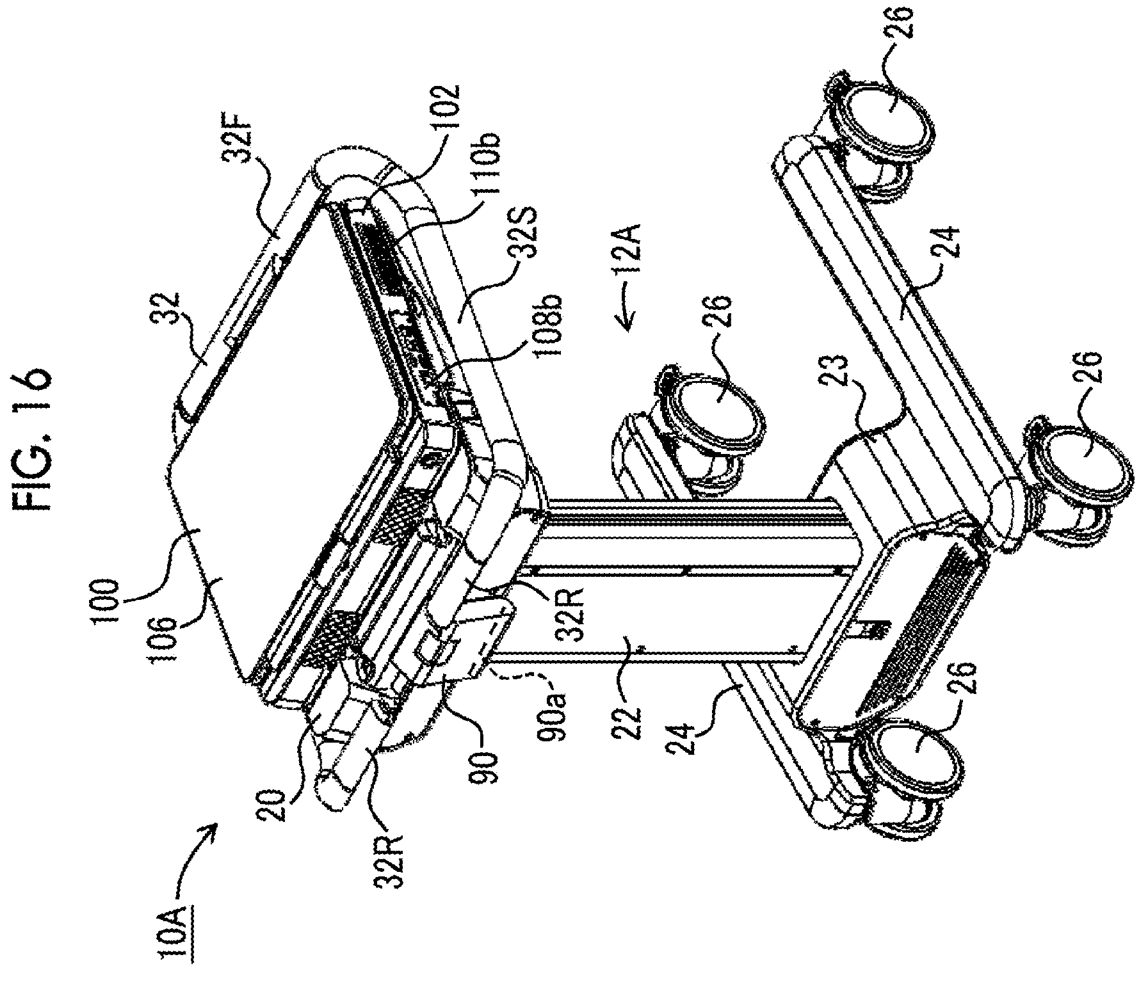
FIG. 16 is a perspective view of a rear surface and a left side surface of the other ultrasound diagnostic unit, and showing a state in which the display portion of the ultrasound diagnostic apparatus is closed.

Next, an ultrasound diagnostic unit of another embodiment will be described. FIGS. 15 and 16 are perspective views of another ultrasound diagnostic unit 10A. In these figures, a state where the display portion 106 of the ultrasound diagnostic apparatus 100 is closed is shown. The ultrasound diagnostic unit 10A has a different configuration of the cart 12A from the ultrasound diagnostic unit 10 of the above-described embodiment. Specifically, in the case of the cart 12A in FIGS. 15 and 16, the operation portion for raising and lowering the seat 20 includes only the push-button 50F at the front, and the two lever elements at the rear are omitted. The cart 12A can be realized by omitting the two lever elements 50R of the cart 12 of the above-described embodiment and the mechanism connected to the two lever elements 50R.

In the ultrasound diagnostic unit 10A of this other embodiment as well, the same operational effects as those of the ultrasound diagnostic unit 10 described above can be obtained. For example, the operator can adjust the height of the seat 20 by pressing the push-button 50F with the thumb in a state where the hand is placed on the left portion or the right portion of the front handle 32F. In addition, in a case where the operator of the cart 12 is, for example, behind the cart 12, the operator can extend a hand in front of the cart 12 and press the push-button 50F to adjust the height of the seat 20.

What is claimed is:

1. A cart for an ultrasound diagnostic apparatus comprising:

a seat on which a portable ultrasound diagnostic apparatus is placed;

a handle connected to the seat;

a columnar support that supports the seat to be raisable and lowerable;

a raising and lowering operation portion for raising and lowering the seat;

a plurality of leg portions that support the columnar support; and casters disposed on the leg portions, wherein the handle includes a front handle disposed in front of the seat and a rear handle disposed behind the seat, the raising and lowering operation portion includes a front operation portion disposed below the front handle and a rear operation portion disposed below the rear handle, the front operation portion is a push-button disposed below a center of the front handle in a lateral direction, the rear operation portion is a lever disposed below the rear handle, the columnar support includes a gas spring having an unlocking pin, and wherein pressing the push-button and pulling up the lever each cause the unlocking pin to change from a non-operative state to an operative state so that the seat is unlocked from a locked state in which the seat is unraisable and unlowerable.

2. The cart for an ultrasound diagnostic apparatus according to claim 1, wherein the lever includes two lever elements, the two lever elements are disposed at interval in a lateral direction, and the seat locked to be unraisable and unlowerable is unlocked in a case where at least one of the two lever elements is pulled up.

3. The cart for an ultrasound diagnostic apparatus according to claim 1, wherein the columnar support further includes an upper columnar support to which the seat is connected, and a lower columnar support disposed below the upper columnar support, the gas spring disposed inside the upper columnar support and the lower columnar support, the columnar support has a structure that expands and contracts by one of the upper columnar support or the lower columnar support being inserted into the other, one end of the gas spring is fixed to the seat, and the other end is fixed to the lower columnar support or a support body disposed below the lower columnar support, the gas spring fixes the seat to the lower columnar support in the non-operative state of the unlocking pin, the gas spring releases the fixing of the seat to the lower columnar support in the operative state of the unlocking pin and biases the seat upward with respect to the lower columnar support, and the front operation portion or the rear operation portion changes the unlocking pin from the non-operative state to the operative state by being operated.

4. The cart for an ultrasound diagnostic apparatus according to claim 2, wherein the columnar support further includes an upper columnar support to which the seat is connected, and a lower columnar support disposed below the upper columnar support, the gas spring disposed inside the upper columnar support and the lower columnar support, the columnar support has a structure that expands and contracts by one of the upper columnar support or the lower columnar support being inserted into the other, one end of the gas spring is fixed to the seat, and the other end is fixed to the lower columnar support or a support body disposed below the lower columnar support, the gas spring fixes the seat to the lower columnar support in the non-operative state of the unlocking pin, the gas spring releases the fixing of the seat to the lower columnar support in the operative state of the unlocking pin and biases the seat upward with respect to the lower columnar support, and the front operation portion or the rear operation portion changes the unlocking pin from the non-operative state to the operative state by being operated.

5. The cart for an ultrasound diagnostic apparatus according to claim 1, wherein the handle further includes side handles disposed on right and left sides of the seat, and the handle is connected to surround the seat.

6. The cart for an ultrasound diagnostic apparatus according to claim 2, wherein the handle further includes side handles disposed on right and left sides of the seat, and the handle is connected to surround the seat.

7. An ultrasound diagnostic unit comprising:

the cart for an ultrasound diagnostic apparatus according to claim 1; and the portable ultrasound diagnostic apparatus placed on the seat of the cart.

8. An ultrasound diagnostic unit comprising:

the cart for an ultrasound diagnostic apparatus according to claim 2; and the portable ultrasound diagnostic apparatus placed on the seat of the cart.

* * * * *